(12) United States Patent
Robson et al.

(10) Patent No.: US 11,434,435 B2
(45) Date of Patent: Sep. 6, 2022

(54) ONLINE ZETA-POTENTIAL MEASUREMENTS FOR OPTIMIZATION OF EMULSION BREAKER DOSAGE IN ETHYLENE PLANTS

(71) Applicant: SABIC Global Technologies B.V., Bergen op Zoom (NL)

(72) Inventors: Ian Robson, Redcar (GB); Fabrice Cuoq, Geleen (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 214 days.

(21) Appl. No.: 16/328,092

(22) PCT Filed: Aug. 22, 2017

(86) PCT No.: PCT/IB2017/055060
§ 371 (c)(1),
(2) Date: Feb. 25, 2019

(87) PCT Pub. No.: WO2018/037339
PCT Pub. Date: Mar. 1, 2018

(65) Prior Publication Data
US 2019/0185763 A1 Jun. 20, 2019

Related U.S. Application Data

(60) Provisional application No. 62/378,287, filed on Aug. 23, 2016.

(51) Int. Cl.
C10G 33/08 (2006.01)
C10G 33/04 (2006.01)
(Continued)

(52) U.S. Cl.
CPC ............... *C10G 33/08* (2013.01); *C02F 1/40* (2013.01); *C07C 7/20* (2013.01); *C10G 33/04* (2013.01);
(Continued)

(58) Field of Classification Search
CPC ........ C10G 33/08; C10G 33/04; C10G 75/04; C10G 2300/1092; C10G 2300/301;
(Continued)

(56) References Cited

U.S. PATENT DOCUMENTS 5,294,347 A * 3/1994 Byrne ................ C02F 1/54
  210/708
5,545,238 A * 8/1996 Brooker ................ C10J 3/466
  252/373

(Continued)

FOREIGN PATENT DOCUMENTS

CN    101837264 A    9/2010
CN    203144205 U    8/2013
(Continued)

OTHER PUBLICATIONS

Nguyen et al ("Chemical Interactions and Demulsifier Characteristics for Enhanced Oil Recovery Applications", | Energy Fuels 2012, 26, 2742-2750). (Year: 2012).*

(Continued)

*Primary Examiner* — Robert S Jones, Jr.
*Assistant Examiner* — Jiangtian Xu
(74) *Attorney, Agent, or Firm* — Norton Rose Fulbright US LLP

(57) ABSTRACT

A method for treating an emulsion emanating from a quenching process in production of ethylene that includes online monitoring of zeta potential of the hydrocarbon/water emulsion in a quench water tower and/or a quench water loop. In response to the online monitoring of zeta potential, (Continued)

the method changes the amount of demulsifier being added to the hydrocarbon/water emulsion such that the amount of demulsifier is effective in breaking the emulsion.

19 Claims, 6 Drawing Sheets

(51) Int. Cl.

| | | |
|---|---|---|
| *C10G 75/04* | (2006.01) | |
| *C02F 1/40* | (2006.01) | |
| *C07C 7/20* | (2006.01) | |
| *C02F 101/32* | (2006.01) | |
| *C02F 103/38* | (2006.01) | |
| *C02F 1/00* | (2006.01) | |
| *C02F 103/36* | (2006.01) | |

(52) U.S. Cl.
CPC ........ *C10G 75/04* (2013.01); *C02F 2001/007* (2013.01); *C02F 2101/325* (2013.01); *C02F 2103/36* (2013.01); *C02F 2103/38* (2013.01); *C02F 2209/006* (2013.01); *C10G 2300/1092* (2013.01); *C10G 2300/301* (2013.01); *C10G 2300/4075* (2013.01); *C10G 2300/4081* (2013.01); *C10G 2300/80* (2013.01); *C10G 2400/20* (2013.01)

(58) Field of Classification Search
CPC .... C10G 2300/4075; C10G 2300/4081; C10G 2300/80; C10G 2400/20; C02F 1/40; C02F 2001/007; C02F 2101/325; C02F 2103/36; C02F 2103/38; C02F 2209/006; C07C 7/20
See application file for complete search history.

(56) References Cited

U.S. PATENT DOCUMENTS

| | | | | |
|---|---|---|---|---|
| 10,047,301 B2* | 8/2018 | Cuoq | .................. | B01D 17/047 |
| 2006/0289359 A1* | 12/2006 | Manek | ..................... | C02F 1/682 |
| | | | | 210/708 |
| 2015/0315486 A1* | 11/2015 | Yusuf | ..................... | C10G 33/04 |
| | | | | 516/141 |
| 2017/0101589 A1* | 4/2017 | Cuoq | ........................ | C02F 1/68 |
| 2019/0185763 A1* | 6/2019 | Robson | .................. | C10G 33/04 |

FOREIGN PATENT DOCUMENTS

| | | | |
|---|---|---|---|
| CN | 103278535 | A | 9/2013 |
| EP | 0464957 | A2 | 1/1992 |

OTHER PUBLICATIONS

"Introducing the new On-Line Zetasizer WT!—zeta potential clarifies coagulant dosing." Malvern, http://www.malvern.com/en/support/events-and-training/webinars/W150617WaterTreatmentZetasizerWT. aspx, Obtained Aug. 2, 2016, 1 page.
International Search Report and Written Opinion from PCT/IB2017/055060 dated Dec. 12, 2017.
James et al. "Using zeta potential to determine coagulant and polymer dosage." Environmental Science & Engineering magazine, Apr. 10, 2016, 10 pages.
Jefferson et al. "The role of zeta potential in water treatment process control." Malvern Instruments Worldwide, 2015, 6 pages.
Sharp, Emma. "Using online zeta potential measurements for coagulation control: A first for the UK Water Industry." Presentation. NOM 6 IWA Specialist Conference on Natural Organic Matter in Drinking Water, Malvern, Sep. 2015, 24 pages.
Water Treatment Solutions, Increasing the Efficiency and Stability of Water Treatment Processes. Brochure. Malvern, Material relationships. 8 pages.
Woodard, Frank. *Industrial Waste Treatment Handbook*. Woodard & Curran, Butterworth Heinemann, 2001.
Zetasizer WT, On-line zeta potential sensor for water treatment dosage control. Brochure. Malvern, Malvern Instruments Worldwide. 2014. 2 pages.
"Treatment Technology of Three Wastes in Chemical Industry." Edited by Petrochemical Technology Information Station of Liaoning Province, pp. 314-315, 1983. With Translation.
Li et al. "Ethylene Production and Management." China Petrochemical Press, p. 245, Aug. 1992. With Translation.

* cited by examiner

ONLINE ZETA-POTENTIAL MEASUREMENTS FOR OPTIMIZATION OF EMULSION BREAKER DOSAGE IN ETHYLENE PLANTS

CROSS-REFERENCE TO RELATED APPLICATIONS

This application is a national phase application under 35 U.S.C. § 371 of International Application No. PCT/IB2017/055060 filed Aug. 22, 2017, which claims priority to United States Provisional Patent Application No. 62/378,287 filed Aug. 23, 2016. The entire contents of each of the above-referenced disclosures is specifically incorporated by reference herein without disclaimer.

TECHNICAL FIELD

The present invention relates to using online zeta potential measurements to improve emulsion breaker (demulsifier) dosing rates in a water loop used in the production of ethylene.

BACKGROUND OF THE INVENTION

Ethylene is a common building block for a variety of petrochemicals. One way of producing ethylene is to steam crack hydrocarbon feedstocks such as naphtha, ethane, and propane. In the steam cracking (pyrolysis) process, the hydrocarbons are superheated in a reactor to temperatures as high as 750-950 ° C. For the cracking process, a dilution steam generator (DSG) supplies dilution steam to the reactor to reduce the partial pressure of the hydrocarbons. The superheated hydrocarbons are then rapidly cooled (quenched) to stop the reactions after a certain point to optimize cracking product yield. The quenching of the superheated gas in many processes is carried out using water in a quench water tower (QWT). The superheated cracked gas (including ethylene) is flowed into the bottom of the quench water tower and, at the same time, water is sprayed into the top of the quench water tower. As the water in the quench water tower falls, it makes contact with the upwardly flowing superheated cracked gas and, in that way, cools the superheated cracked gas (that includes ethylene) and dilution steam.

Because of the direct contact between the superheated cracked gas in the quench water tower and the condensation of the dilution steam, the water flowing from the quench water tower is mixed with condensed hydrocarbons (referred to as pyrolysis gasoline). Pyrolysis gasoline may include components such as aromatics, olefins, and/or diolefins, among others. In the quench water tower, the pyrolysis gasoline and water mixes and can form an emulsion. Thus, the quench water tower effluent stream flowing from the bottom of the quench water tower may include an emulsion having a hydrocarbon phase dispersed in the water phase. Hydrocarbon in water emulsions are particularly difficult to break. In other words, the emulsion is stable because, once the emulsion is formed, the water does not easily separate from the pyrolysis gasoline.

To facilitate the separation of the water from the pyrolysis gasoline, the quench water tower effluent stream is flowed from the quench water tower to a quench water settler (QWS). At the quench water settler, the quench water effluent stream (including the emulsion) is settled and water is drawn off from the quench water settler. Then, the water from the quench water settler is sent to a process water stripper (PWS). The process water stripper strips the water of acid gases and dissolved hydrocarbons. After being stripped in the process water stripper, the water is routed to the dilution steam generator (mentioned above). The water that is used to generate dilution steam for the cracking furnaces, and subsequently condensed in the quench water tower, is then circulated to the quench water settler, then to the process water stripper, and finally back to the dilution steam generator is referred to as process water, which circulates in a quench water tower loop. The quench water tower, quench water settler, process water stripper, and dilution steam generator are collectively referred to as the dilution steam system (DSS).

Because the emulsion in the quench water tower tends to be stable, the attempt to separate pyrolysis gasoline from water in the quench water tower and/or quench water tower settler is often ineffective and can be time consuming and costly. Consequently, the process water may carry a large amount of hydrocarbons to the process water stripper, which causes fouling of the process water stripper. The dilution steam generator may also foul because of hydrocarbons carry-over. Further, process water that flows from the bottom of the quench water tower and the quench water settler can contain traces of styrene as well as oligomers of styrene that form in the water as a result of the long residence time of the water recycle in the quench water tower loop. These oligomers grow further at process water stripper conditions and cause fouling in the dilution steam system generally.

Fouling at the bottom of the process water stripper and in the dilution steam generator preheaters can lead to poor energy efficiency and, in a worst case scenario, to a plant shutdown, if excessive fouling sufficiently restricts flow of process water in the quench water tower loop. Moreover, fouling of the dilution steam generators can cause cycles of the dilution steam generator to be low (e.g., 4-5 cycles), which can cause water, energy, and chemical losses.

The difficulty in breaking the emulsion in the quench water tower or quench water settler emulsion is often exacerbated by high pH existing in that equipment. Thus, some ethylene plants use an acidic treatment process to control the pH in the quench water tower or quench water settler. Another method for solving the fouling problem is to inhibit polymerization within the quench water tower loop using stable free radical (SFR) type of inhibitors. This helps to inhibit the formation of oligomers and thus improves the quality of the water entering the dilution steam system. A further method for solving the fouling by hydrocarbons is to apply a dispersant in the process water stripper. However, this method has limited effect when the amount of hydrocarbons in the water is high.

A common method of solving the fouling problem involves the use of emulsion breakers to improve pyrolysis gasoline/water separation in the quench water tower, or quench water settler, or both. The use of emulsion breakers results in cleaner water circulating in the dilution steam system. And this cleaner water in the dilution steam system helps to prevent fouling of equipment in the quench water tower loop. Commonly applied emulsion breakers neutralize the negative charges at the droplet surface and enhance coalescence. Emulsion breaker dosing rates are typically based on experience and are not controlled by measurement of residuals or any physico-chemical parameters of the system. This can lead to inefficient emulsion breaking or over-dosing of the emulsion breakers, both of which can be time consuming and costly on a commercial scale. Over-dosing with emulsion breakers actually worsens the ability of water and pyrolysis gasoline to separate from the emulsion, instead of improving such separation. But controlling the optimum dosage of an emulsion breaker to engender pyrolysis gasoline/water separation is not straight forward because the dosage is dependent on the feedstock and other physicochemical parameters of the water that are continuously changing during operation.

BRIEF SUMMARY OF THE INVENTION

A discovery has been made that solves the aforementioned problems associated with emulsion formulation during ethylene production. In particular, the present invention is premised on an online measurement of zeta-potential in the quench water tower loop of an ethylene plant to diminish the risk of emulsion breaker overdosing by measuring the residual charges on the emulsion. Zeta potential is the force that determines the charge interaction amongst particles in a fluid. Online measurement of the zeta potential of the emulsion in the quench water tower loop leads to better water/pyrolysis gasoline separation, which, in turn, leads to operational benefits for the dilution steam system, including less equipment fouling, and/or a reduction in the consumption of chemicals used as emulsion breakers.

Thus, the present invention is directed to systems and methods that utilize online monitoring of zeta potential of a hydrocarbon/water emulsion to control the dosage rate of a demulsifier (emulsion breaker) being used to treat the emulsion (to break the emulsion) in a quench water tower loop of an ethylene plant.

Embodiments of the invention include a method for treating an emulsion emanating from a quenching process in the production of ethylene. The method includes adding a demulsifier to a hydrocarbon/water emulsion in a quench water tower that is in use for ethylene production and online monitoring of zeta potential of the hydrocarbon/water emulsion in the quench water tower. The method further includes, in response to the online monitoring, changing the amount of demulsifier being added to the hydrocarbon/water emulsion (e.g. changing a unit of weight or unit of volume of demulsifier added to a unit of weight or unit of volume of hydrocarbon/water emulsion) such that the amount of demulsifier is effective in breaking the emulsion. In other words, embodiments of the invention ensure sufficient demulsifier, but not too much demulsifier, is provided to break the emulsion.

Embodiments of the invention include a method for treating an emulsion emanating from a quenching process in the production of ethylene. The method includes adding a demulsifier to a hydrocarbon/water emulsion in a quench water tower that is in use for ethylene production and online monitoring of zeta potential of the hydrocarbon/water emulsion in the quench water tower. The method may further include online monitoring of one or more physicochemical parameters of a hydrocarbon stream flowing into the quench water tower. In response to the online monitoring of zeta potential of the hydrocarbon/water emulsion and the online monitoring of the one or more physicochemical parameters, the method includes changing the amount of demulsifier being added to the hydrocarbon/water emulsion so that the zeta potential of the emulsion is within a range of −30−+30 mV.

Embodiments of the invention include a method for treating an emulsion emanating from a quenching process in the production of ethylene. The method includes adding a first demulsifier to a hydrocarbon/water emulsion in a quench water tower and/or quench water loop in use for ethylene production and online monitoring of zeta potential of the hydrocarbon/water emulsion in the quench water tower. In response to the online monitoring of zeta potential of the hydrocarbon/water emulsion, the method may involve changing the amount of the first demulsifier being added to the hydrocarbon/water emulsion in the quench water tower. The method may also include flowing effluent from the quench water tower to a quench water settler. The method may further include adding a second demulsifier to the effluent from the quench water tower and online monitoring of the zeta potential of the effluent from the quench water tower. In response to the online monitoring of the zeta potential of the effluent from the quench water tower, the method may further include changing the amount of the second demulsifier being added to the effluent from the quench water tower.

Non-limiting emulsion breakers that can be used in the context of the present invention include quaternary ammonium salts, quaternized alkanolamine esters, polyethylene glycol/polypropylene glycol triblock copolymers derivatives of amines, polyamines, alkoxylated or polyalkoxylated derivatives of amines, polyethylene imines, polycyanoguanidine, polyaluminum chloride silicate, or any combination thereof. Non-limiting examples of cationic emulsion breakers include polyalkylenepolyamine, epichlorohydrin dimethylamine (EPI-DMA), polydiallyldimethylammonium chloride (polyDADMAC), dimethylaminoethylacrylate methyl chloride salt (DMAEA.MCQ), dimethylaminoethylmethacrylate methyl chloride salt (DMAEM.MCQ), dimethylaminoethylmethacrylate methyl sulfate salt (DMAEM.MSQ), dimethylaminoethylmethacrylate benzyl chloride salt (DMAEM.BCQ), dimethylaminoethylacrylate methyl sulfate salt (DMAEA.MSQ), dimethylaminoethylacrylate benzyl chloride salt (DMAEA.BCQ), methacrylamidopropyl trimethylammonium chloride (MAPTAC), and acrylamidopropyl trimethylammonium chloride (APTAC). In preferred instances, the emulsion breaker can be a cationic emulsion breaker, non-limiting examples of which include polydiallydimethylammonium chloride (polyDADMAC) sold under the tradename of Nalco® 8103 by Nalco Chemical Company (U.S.A.).

The following includes definitions of various terms and phrases used throughout this specification.

"Online monitoring" as the phrase is used in the specification and the claims means automated measurement, of a feature of subject material flowing in a process, by a computerized device, where a portion of the computerized device is located within the process such that the subject material, as it flows in the process, makes contact with the portion of the computerized device and the computerized device is adapted to take measurements of the subject material.

The term "emulsion" encompasses systems having at least two phases, a continuous phase and a dispersed phase. By way of example, the continuous phase can be an aqueous phase such as water, and the dispersed phase can be an organic phase such as a hydrocarbon phase (i.e., a hydrocarbon-in-water emulsion). The continuous and dispersed phases are typical liquid phases, although one phase could be a solid phase.

The terms and phrases "emulsion breaking," "demulsifying," or "demulsification" includes separating at least two phases of an emulsion (e.g., separating a hydrocarbon phase from an aqueous phase). Emulsion breaking can occur when the factors that stabilize the emulsion are disrupted to allow the emulsified droplets (i.e., the dispersed phase) to coalesce. The accumulated electric charges on the emulsified droplet can be neutralized by introducing a charge opposite to that of the droplet. By way of example, cationic demulsifiers include compounds having a positive charge that can neutralize negatively charged components of the emulsion to destabilize the emulsion and cause phase separation or emulsion breaking.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc. disclosed throughout the specification.

In the context of the present invention, embodiments 1-20 are described. Embodiment 1 is a method for treating an emulsion emanating from a quenching process in production of ethylene. The method includes adding a demulsifier to a hydrocarbon/water emulsion in a quench water tower in use for ethylene production; online monitoring of zeta potential of the hydrocarbon/water emulsion in the quench water tower; and in response to the online monitoring of zeta potential, changing the amount of demulsifier being added to the hydrocarbon/water emulsion such that the amount of demulsifier is effective in breaking the emulsion. Embodiment 2 is the method of Embodiment 1, wherein the amount of demulsifier is changed so that the zeta potential of the emulsion is within a range of −30 to +40 mV. Embodiment 3 is the method of Embodiments 1 or 2, wherein the amount of demulsifier is changed so that the zeta potential of the emulsion is within a range of −5 to +5 mV. Embodiment 4 is the method of any of Embodiments 1 to 3, further including the step of monitoring of one or more physicochemical parameters of a hydrocarbon stream flowing into the quench water tower. Embodiment 5 is the method of Embodiment 4, wherein the one or more physicochemical parameters is selected from the list consisting of: boiling point, critical point, surface tension, and vapor pressure. Embodiment 6 is the method of any of Embodiments 4 or 5, further including, in response to the monitoring of the one or more physicochemical parameters and the online monitoring of zeta potential, changing the amount of demulsifier being added to the hydrocarbon/water emulsion such that the amount of demulsifier is effective in breaking the emulsion. Embodiment 7 is the method of Embodiments 1 to 6, wherein the amount of demulsifier being changed is changed so that the zeta potential of the emulsion is within a range of −30 to +40 mV. Embodiment 8 is the method of any of Embodiments 1 to 7, wherein the amount of demulsifier is changed so that the zeta potential of the emulsion is within a range of −5 to +5 mV. Embodiment 9 is the method of any of Embodiments 1 to 8, wherein the demulsifier is added at a point in the quench water tower such that the demulsifier is effective in breaking the hydrocarbon/water emulsion in the quench water tower. Embodiment 10 is the method of any one of Embodiments 1 to 9, wherein the demulsifier comprises a cationic demulsifier.

Embodiment 11 is directed to a method for treating an emulsion emanating from a quenching process in production of ethylene, the method including the steps of adding a first demulsifier to a hydrocarbon/water emulsion in a quench water tower in use for ethylene production; online monitoring of zeta potential of the hydrocarbon/water emulsion in the quench water tower; and, in response to the online monitoring of zeta potential of the hydrocarbon/water emulsion, changing the amount of the first demulsifier being added to the hydrocarbon/water emulsion in the quench water tower; flowing effluent from the quench water tower to a quench water settler; online monitoring of zeta potential of the effluent from the quench water tower; adding a second demulsifier to the effluent from the quench water tower; online monitoring of zeta potential of the effluent from the quench water tower; and, in response to the online monitoring of zeta potential of the effluent, changing the amount of the second demulsifier being added to the effluent from the quench water tower. Embodiment 12 is the method of embodiment 11, wherein the amount of the first demulsifier and the second demulsifier are changed so that the zeta potential of the hydrocarbon/water emulsion in the quench water tower and the zeta potential of the effluent from the quench water tower are within a range of −30-+40 mV. Embodiment 13 is the embodiment of any of embodiments 11 and 12 wherein the amount of the first demulsifier and the second demulsifier are changed so that the zeta potential of the hydrocarbon/water emulsion in the quench water tower and the zeta potential of the effluent from the quench water tower are within a range of −5 to +5 mV. Embodiment 14 is the method of any of embodiments 11 to 13, wherein the amount of demulsifier is changed so that the zeta potential of the emulsion is within a range of −5 to +5 mV. Embodiment 15 is the method of any one of Embodiments 11 to 14, wherein the first demulsifier is added at a point in the quench water tower such that the demulsifier is effective in breaking the hydrocarbon/water emulsion in the quench water tower. Embodiment 16 is directed to the method of any one of Embodiments 11 to 15, wherein the second demulsifier is added to the effluent from the quench water tower in the quench water settler. Embodiment 17 is the method of any one of embodiments 11 to 14, wherein the second demulsifier is added to the effluent from the quench water tower before it is fed to the quench water settler. Embodiment 18 is the method of any one of embodiments 11 to 17, wherein at least one of the first demulsifier and second demulsifier comprises a cationic demulsifier. Embodiment 19 is the method of any one of embodiments 11 to 18, wherein the first demulsifier and second demulsifier are different.

Embodiment 20 is the method of any one of embodiments 11 to 19, wherein the first demulsifier and second demulsifier are same.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Figure 1:
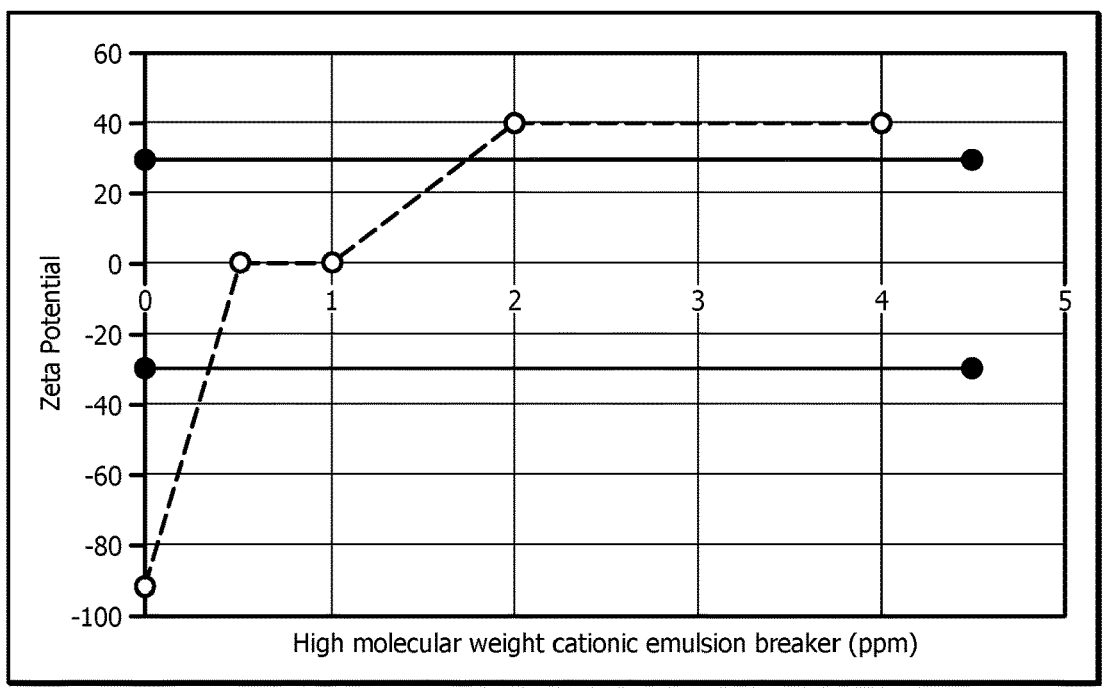
FIG. 1 is a plot of offline measurements of zeta potential of a process water sample from an ethylene plant versus the amount of cationic emulsion breaker added to the process water sample.

Embodiments of the invention include online monitoring of the zeta potential of an emulsion within or downstream a quench water tower of an ethylene plant and using the information gathered from such monitoring to keep the emulsion breaker dosing rate in a range that is most effective in breaking the emulsion. The online monitoring of zeta potential may be performed, for example, by a ZetaSizer WT, which is an online unit commercially available from Malvern Instruments Worldwide. The non-limiting data provided in the Examples and in FIG. 1 illustrates the feasibility of the processes of the present invention.

Quench water can include dissolved and emulsified hydrocarbon compounds (oils), as well as heavy tar-like polymers and coke particulate matter. The hydrocarbon oils can include hydrocarbons, aromatic hydrocarbons and low molecular weight polymers. These materials form stable oil/water emulsions when the cracked gas stream is intimately mixed with the quench water. More specifically, quench water can include traces of styrene, and oligomers of styrene that originate from the long residence time due to water recycle in the quench tower loop. The resulting emulsions can include about 100 to 10,000 parts hydrocarbon compounds per million parts emulsion. The stability of the emulsion can be due to a mutual affinity between the unsaturated hydrocarbon components in the dispersed oil phase and the continuous aqueous phase. Thus, the emulsion will resist efforts to separate it sharply into its various phases.

To improve the hydrocarbon/water separation in the quench water or quench water settler and to bring about cleaner process water within the dilution steam system, an emulsion breaker may be applied, for example, at the feed of the quench water settler or bottom of the quench water tower (or other points within the quench water tower loop). Optimal water/hydrocarbon separation in a quench water tower loop usually demands dosing of the emulsion in the quench water tower loop within a narrow window of dosing rates.

Embodiments of the invention are directed to providing the optimal amount of emulsion breaker (e.g. cationic emulsion breakers) by using online zeta potential measurements to optimize the gasoline/water separation and therefore increase the dilution steam system/dilution steam generator run length. In embodiments of the invention a zeta-potential range of −30 mV and +40 mV is optimal for emulsion breaking. In embodiments of the invention a zeta-potential range of −30 mV and +30 mV is optimal for emulsion breaking, with −10 mV to +10 my being preferred, −5 mV to +5 mV being more preferred, and around 0 being most preferred.

Figure 2:
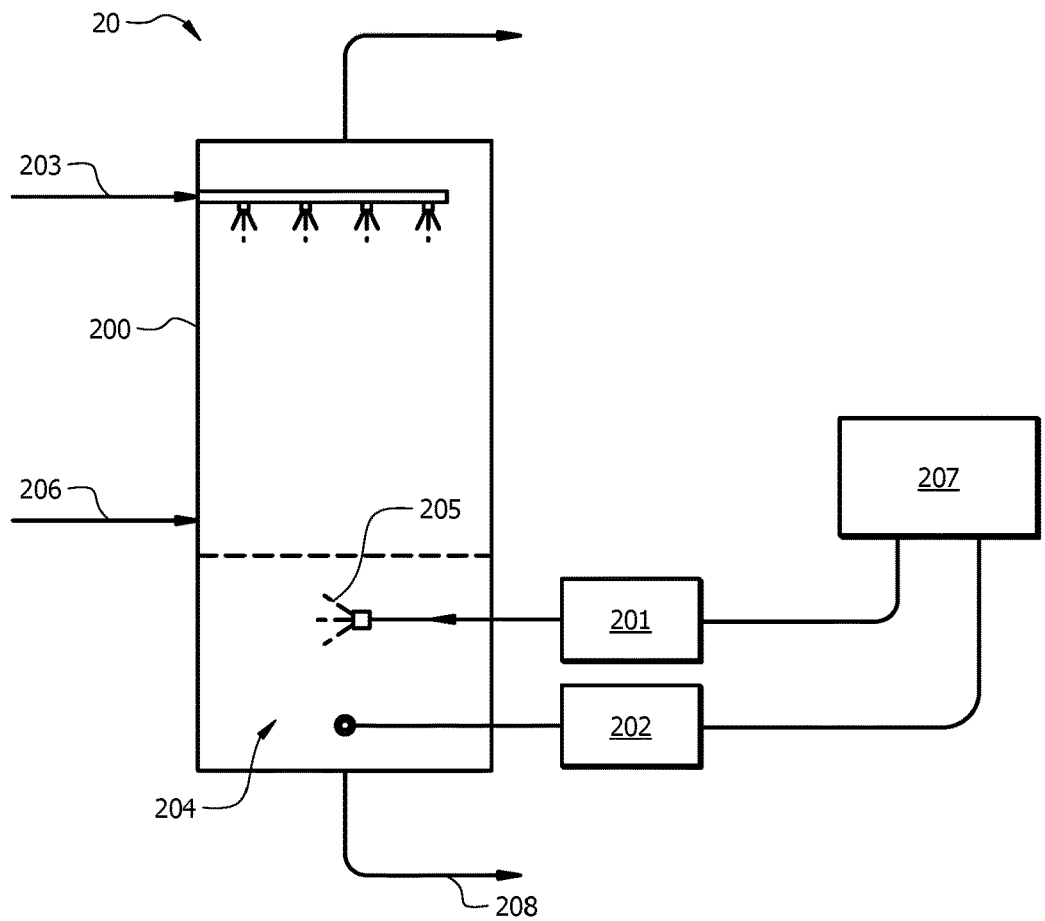
FIG. 2 shows a system for treating an emulsion emanating from a quenching process in the production of ethylene, according to embodiments of the invention.
Figure 3:
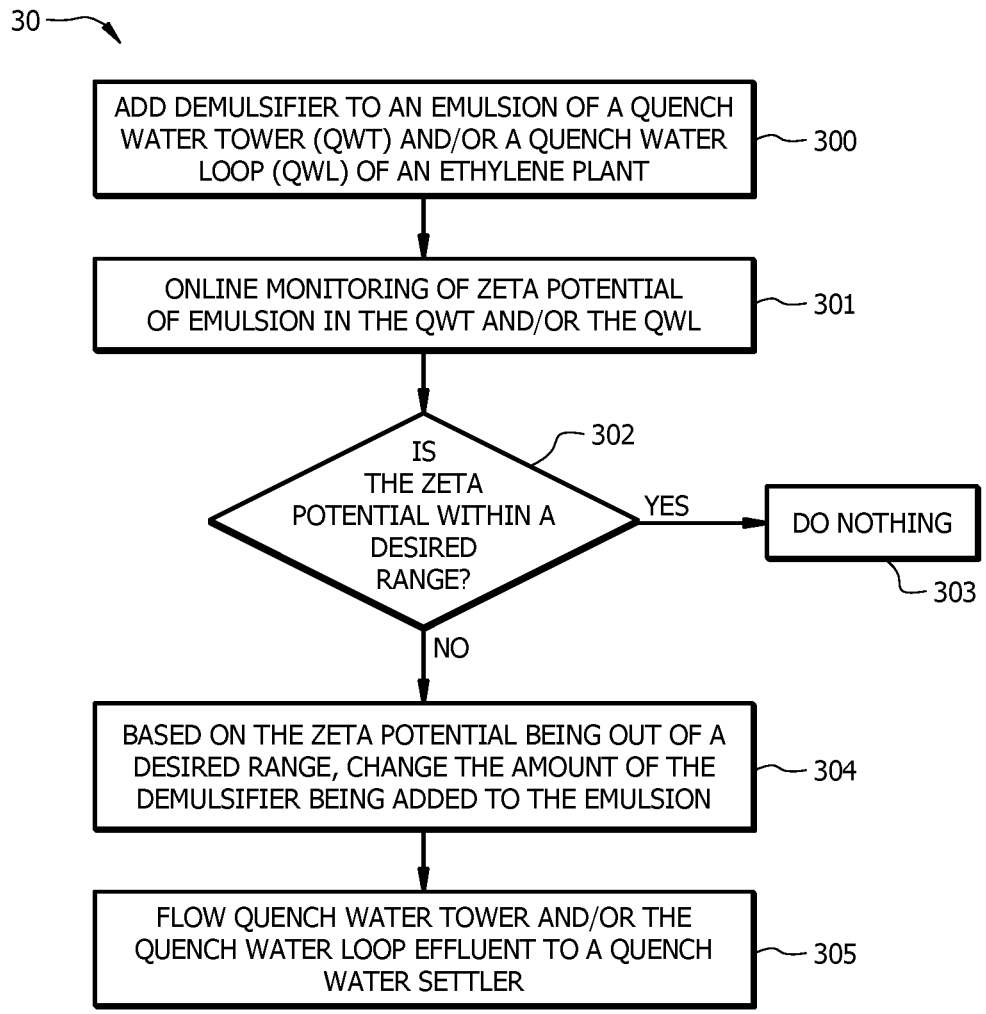
FIG. 3 shows a method that may be used for treating an emulsion emanating from a quenching process in the production of ethylene, according to embodiments of the invention.

FIG. 2 shows system 20 for treating an emulsion emanating from a quenching process in the production of ethylene, according to embodiments of the invention. FIG. 3 shows 30 method, which may be used for treating an emulsion emanating from a quenching process in the production of ethylene, according to embodiments of the invention. Method 30 may be implemented using system 20. System 20 includes quench water tower 200, treating unit 201, online zeta potential monitor 202, and controller 207. Cracked gas 206 flows from a steam cracking furnace into the bottom of quench water tower 200. Concurrently, quench water 203 is sprayed into the top of quench water tower 200. Contact between cracked gas 206, condensed dilution steam, and quench water 203 forms emulsion 204 in quench water tower 200.

Treating unit 201 treats emulsion 204 in quench water tower 200 with demulsifier 205 (emulsion breaker). Thus, treating unit 201 may be used to implement an aspect of method 30, namely, adding demulsifier 205 to emulsion 204 in quench water tower 200 and/or a quench water loop in use for ethylene production, as shown at block 300 of FIG. 3. In embodiments of the invention, demulsifier 205 is added at a point in quench water tower 200 and/or the quench water loop such that demulsifier 205 is most effective in breaking emulsion 204. Depending on the design of quench water tower 200 and/or the quench water loop, the point of addition of demulsifier 205 may vary. Tests may be carried out to determine what point of addition of demulsifier 205 to quench water tower 200 and/or the quench water loop is most effective in breaking emulsion 204. Online zeta potential monitor 202 can be configured to automatically make measurements of emulsion 204 in quench water tower 200 and/or the quench water loop while emulsion 204 is flowing through quench water tower 200 and/or the water quench loop. For example, in embodiments of the invention, a measurement of zeta potential of emulsion 204 may be made periodically, where the period is in the range of 30 seconds to 20 minutes (e.g. the period may be 30 seconds, 1 min., 2 mins., 3 mins., 4 mins., 5 mins., 6 mins., 7 mins., 8 mins., 9 mins., 10 mins., 11 mins., 12 mins., 13 mins., 14 mins., 15 mins., 16 mins., 17 mins., 18 mins., 19 mins., or 20 mins). In this way, for method 30, online zeta potential monitor 202 provides online monitoring of zeta potential of emulsion 204 in quench water tower 200 and/or the quench water loop, as shown at block 301 (FIG. 3). It should be noted that online zeta potential monitor 202 can be online such that it is adapted to directly measure the zeta potential of emulsion 404 while emulsion 404 is circulating in the quench water tower loop, at whatever frequency desired. Online zeta potential monitor 202 may be disposed in the process such that online zeta potential monitor 202 is in direct contact with emulsion 204. For example, online zeta potential monitor 202 may be configured such that emulsion 204 flows through a portion of online zeta potential monitor 202 and that portion captures an aliquot from emulsion 204; and online zeta potential monitor 202 measures the zeta potential of the aliquot. Online monitoring described herein is opposed to offline monitoring of zeta potential that may involve, for example, taking samples from the quench water tower and/or the quench water loop to a laboratory for analysis.

FIG. 2 shows online zeta potential monitor 202 downstream of treating unit 201, according to the flow of emulsion 204. Thus, online zeta potential monitor 202 is in a reactive configuration in relation to the treating unit 201. In other words, after treating unit 201 treats emulsion 204, online zeta potential monitor 202 analyzes that treated emulsion and it is determined whether the zeta potential is in the desired range, and, if not, treating unit 201 makes an adjustment to the dosing rate so that the zeta potential of emulsion 204 falls within a desired range. Alternatively or additionally, in embodiments of the invention, one or more online zeta potential monitors may be upstream of treating unit 201, according to the flow of emulsion 204. Thus, the one or more online zeta potential monitors would be in a predictive configuration in relation to treating unit 201. In other words, before treating unit 201 treats emulsion 204, the one or more online zeta potential monitors analyzes the untreated emulsion and it is determined whether the zeta potential is in the desired range, and, if not, treating unit 201 treats emulsion 204 at a particular dosing rate so that the zeta potential of the emulsion falls within a desired range. Measurements of the zeta potential of emulsion 204 are used to change the amount of demulsifier 205 being added to emulsion 204 such that the amount of demulsifier is effective in breaking emulsion 204. For example, in embodiments of the invention, after online zeta potential monitor 202 automatically makes the measurements of the zeta potential of emulsion 204, the measurements are sent to a processor of a computer (e.g. processor or controller 207) that analyzes whether the dosing rate of demulsifier 205 is optimal, at block 302 (FIG. 3). Specifically, controller 207 may determine whether the zeta potential is within a desired range (e.g. a range in which emulsion 204 is least stable and in which demulsifier 205 is most effective in breaking emulsion 204). If the zeta potential is within the desired range, block 303 provides that nothing is done. If the zeta potential is not within the desired range, at block 304, controller 207 instructs treating unit 201 to change the dosing rate to put the zeta potential of emulsion 204 in the desired range and thereby achieve an effective dosing rate for breaking emulsion 204. Block 305 provides that quench water tower effluent 208 and/or quench water loop effluent is routed to a quench water settler.

In embodiments of the invention, by changes in the dosing rate of the demulsifier, the zeta potential of the emulsion is adjusted to be within an optimal range of −30 to +30 mV, zeta potentials there between (e.g. −29 mV, −28 mV, −27 mV, −26 mV, −25 mV, −24 mV, −23 mV, −22 mV, −21 mV, −20 mV, −19 mV, −18 mV, −17 mV, −16 mV, −15 mV, −14 mV, −13 mV, −12 mV, −11 mV, −10 mV, −9 mV, −8 mV, −7 mV, −6 mV, −5 mV, −4 mV, −3 mV, −2 mV, −1 mV, 0 mV, 1 mV, 2 mV, 3 mV, 4 mV, 5 mV, 6 mV, 7 mV, 8 mV, 9 mV, 10 mV, 11 mV, 12 mV, 13 mV, 14 mV, 15 mV, 16 mV, 17 mV, 18 mV, 19 mV, 20 mV, 21 mV, 22 mV, 23 mV, 24 mV, 25 mV, 26 mV, 27 mV, 28 mV, 29 mV, 30 mV), and combinations thereof, but preferably within a range of −5 to +5 mV. Controller 207 may be a part of online zeta potential monitor 202, treating unit 201, or separate from both online zeta potential monitor 202 and treating unit 201 (e.g. controller 207 may be a process control system for the ethylene plant). Method 30, or aspects thereof, may be repeated as often as required and at whatever interval is desired.

Figure 4:
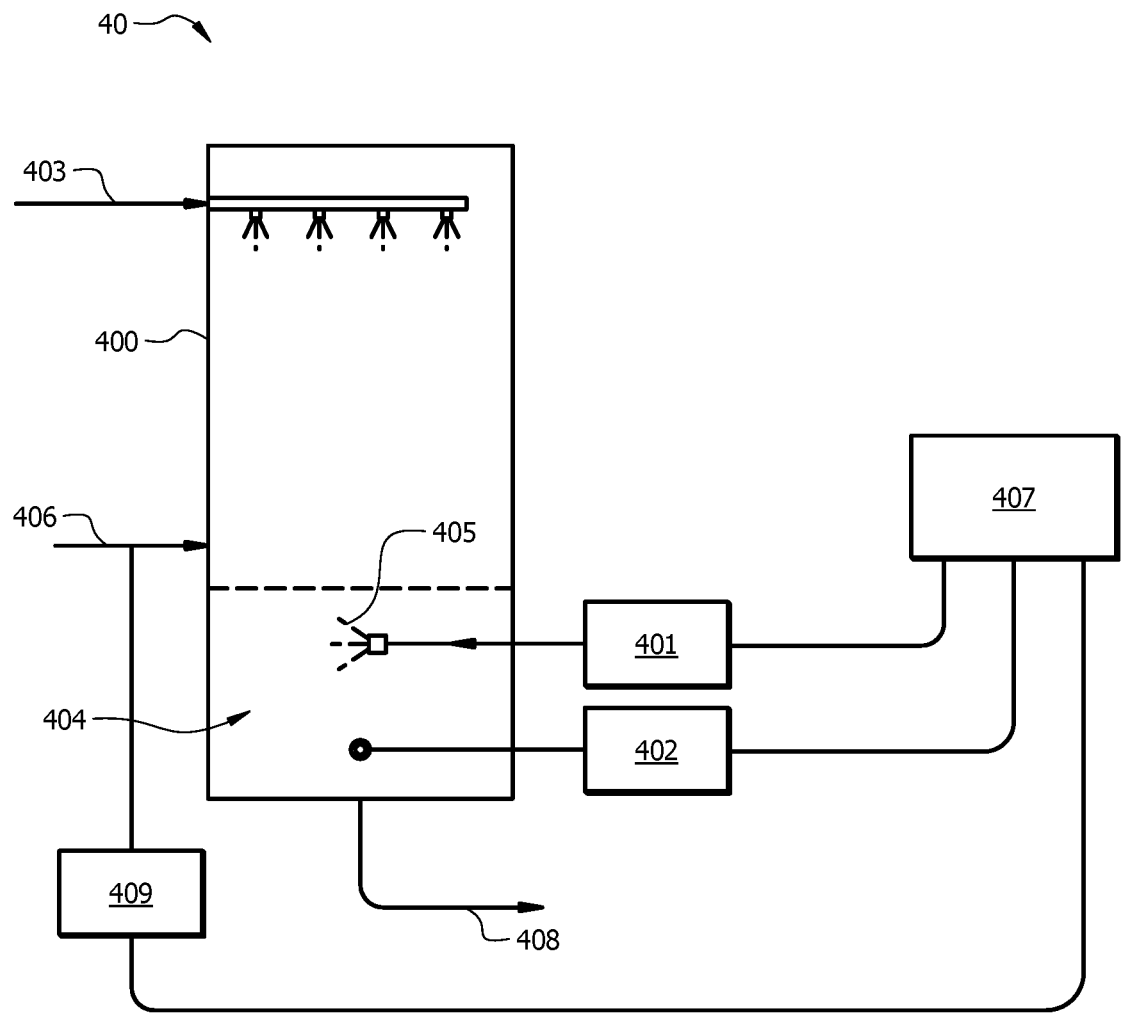
FIG. 4 shows a system for treating an emulsion emanating from a quenching process in the production of ethylene, according to embodiments of the invention.
Figure 5:
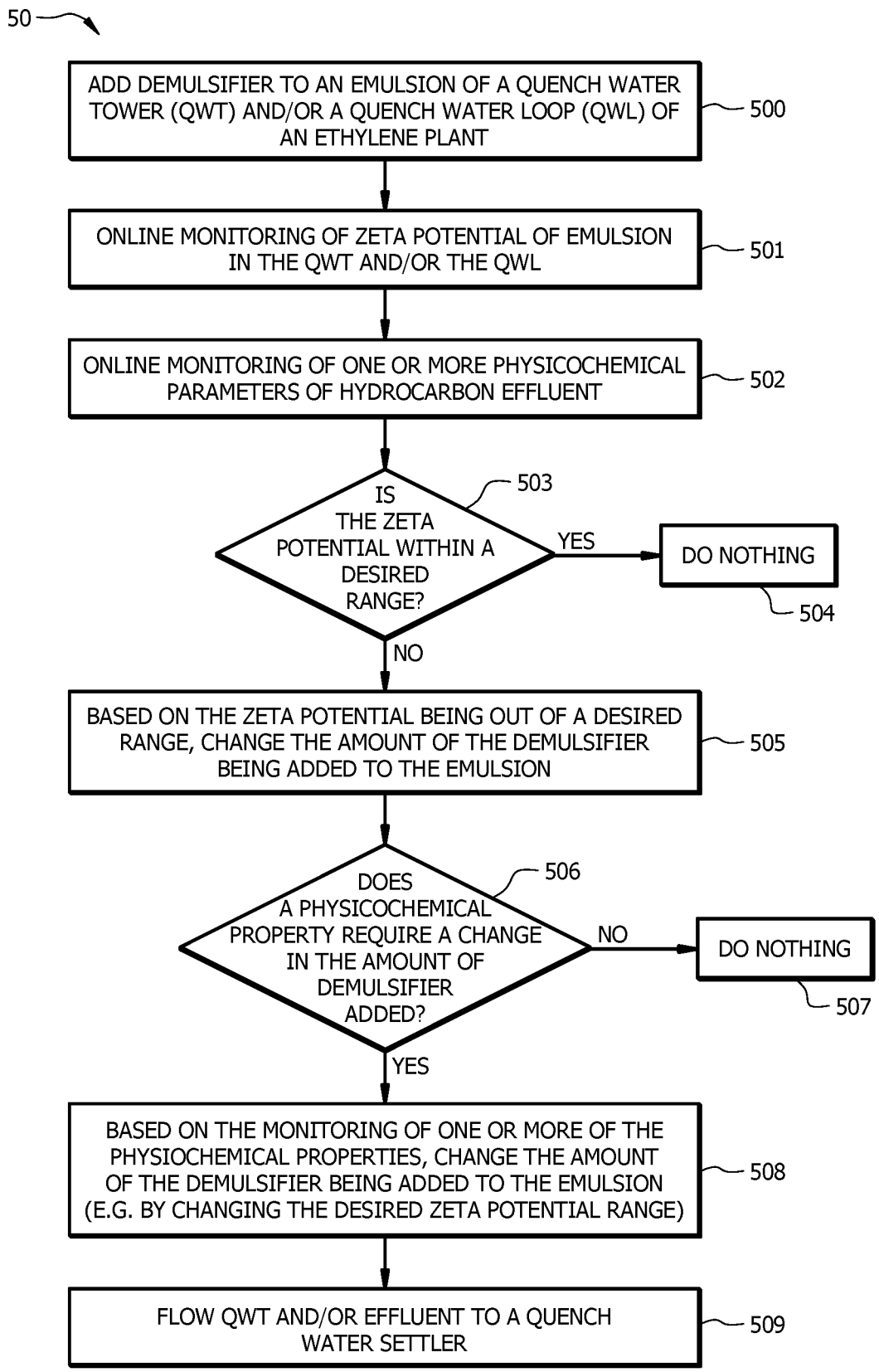
FIG. 5 shows a method that may be used for treating an emulsion emanating from a quenching process in the production of ethylene, according to embodiments of the invention.

FIG. 4 shows system 40 for treating an emulsion emanating from a quenching process in the production of ethylene, according to embodiments of the invention. FIG. 5 shows method 50, which may be used for treating an emulsion emanating from a quenching process in the production of ethylene, according to embodiments of the invention. Method 50 may be implemented using system 40. System 40 includes quench water tower 400, treating unit 401, online zeta potential monitor 402, controller 407, and physicochemical monitor 409. Cracked gas 406 flows from a steam cracking furnace into the bottom of quench water tower 400. Concurrently, quench water 403 is sprayed into the top of quench water tower 400. Contact between cracked gas 406, condensed dilution steam, and quench water 403 forms emulsion 404 in quench water tower 400.

Treating unit 401 treats emulsion 404 in quench water tower 400 with demulsifier 405. Thus, treating unit 401 may be used to implement an aspect of method 50, namely adding demulsifier 405 to emulsion 404 in quench water tower 400, as shown at block 500 of FIG. 5. In embodiments of the invention, demulsifier 405 is added at a point in quench water tower 400 and/or a quench water loop such that demulsifier 405 is most effective in breaking emulsion 404. Depending on the design of quench water tower 400 and/or the quench water loop, the point of addition of demulsifier 405 may vary. Tests may be carried out to determine what point of addition of demulsifier 405 to quench water tower 400 and/or the quench water loop is most effective in breaking emulsion 404. Online zeta potential monitor 402 is similar to online zeta potential monitor 202, and thus, zeta potential monitor 402 can automatically make zeta potential measurements of emulsion 404 in quench water tower 400 (block 501, FIG. 5) and/or the quench water loop, in a manner described above in relation to online zeta potential monitor 202 and quench water tower 200 and/or the quench water loop. Method 50 may also include, at block 502, online monitoring of one or more physicochemical parameters, by online physicochemical monitor 409, of cracked gas 406 flowing into quench water tower 400 and/or a quench water loop.

Measurements of the zeta potential of emulsion 404 are used to change the amount of demulsifier 405 being added to emulsion 404 such that the amount of demulsifier is effective in breaking emulsion 404. For example, in embodiments of the invention, after online zeta potential monitor 402 automatically makes the measurements of the zeta potential of emulsion 404, the measurements are sent to a processor of a computer (e.g. processor or controller 407) that analyzes whether the dosing rate of demulsifier 405 is optimal, at block 503 (FIG. 5). Specifically, controller 407 may determine whether the zeta potential is within a desired range (e.g. a range in which emulsion 404 is least stable and in which demulsifier 405 is most effective in breaking emulsion 404). If the zeta potential is within the desired range, block 504 provides that nothing is done. If the zeta potential is not within the desired range, at block 505, controller 407 instructs treating unit 401 to change the dosing rate to put the zeta potential of emulsion 404 in the desired range and thereby achieve an effective dosing rate for breaking emulsion 404.

Measurements of one or more physicochemical parameters of cracked gas 406 flowing into the quench water tower may be used to change the amount of demulsifier 405 being added to emulsion 404 such that the amount of demulsifier is effective in breaking the emulsion 404. In embodiments of the invention, after the measurements of one or more physicochemical parameters of emulsion 404 by physicochemical monitor 409, at block 505, the measurements are sent to a processor of a computer (e.g. processor or controller 407) that analyzes whether the dosing rate of demulsifier 405 needs to be changed (block 506). If the physicochemical measurements do not require any changes to the dosage rate of demulsifier 405, then block 507 provides that nothing is done. If the physicochemical measurements are not within the desired range, at block 508, controller 407 may instruct treating unit 401 to change the dosing rate of demulsifier 405. For example, based on measurements of one or more physicochemical parameters such as boiling point, critical point, surface tension, vapor pressure, density, viscosity etc., controller 407 may instruct treating unit 401 to change the amount of demulsifier 405 being added to emulsion 404. Such instruction may involve changing the desired range of zeta potential based on the measured physicochemical parameters. Measurements of one or more physicochemical parameters of cracked gas 406 may be online or offline measurements.

In embodiments of the invention, controller 407 may perform the steps involved at block 503 and block 506 concurrently to determine what changes may be made to the dosing rate of demulsifier 405. In other words, the online measurements of the zeta potential of emulsion 404 together with the physicochemical measurements of cracked gas 406 may be taken into account to determine if any changes should be made to the dosing rate of demulsifier 405.

It should be noted that FIG. 4 shows physicochemical monitor 409 is upstream of treating unit 401, since physicochemical monitor 409 monitors the physicochemical parameters of cracked gas 406. Thus, physicochemical monitor 409 is in a predictive configuration in relation to treating unit 401. In other words, physicochemical monitor 409 analyzes cracked gas 406 and it is determined whether to change the amount of demulsifier 405 being added to emulsion 404, and, if so, treating unit 401 makes an adjustment to the dosing rate of demulsifier 405 (e.g. by changing the desired zeta potential range, which in turn may cause a change in the amount of demulsifier added).

In embodiments of the invention, based on measurements of one or more physicochemical parameters, the amount of demulsifier added to emulsion 404 is changed so that the zeta potential of the emulsion is within a range of −30 to +30 mV. More preferably, based on measurements of one or more physicochemical parameters, the amount of demulsifier added to emulsion 404 is changed so that the zeta potential of the emulsion is within a range of −5 to +5 mV, or more preferably about 0 mV. Block 509 provides that quench water tower effluent 408 is routed to a quench water settler. Alternatively, the quench water settler is integrated in 400 quench water tower, and the quench water tower effluent 408 is routed to a process water stripper (PWS). Method 50, or aspects thereof, may be repeated as often as required and at whatever interval is desired.

Figure 6:
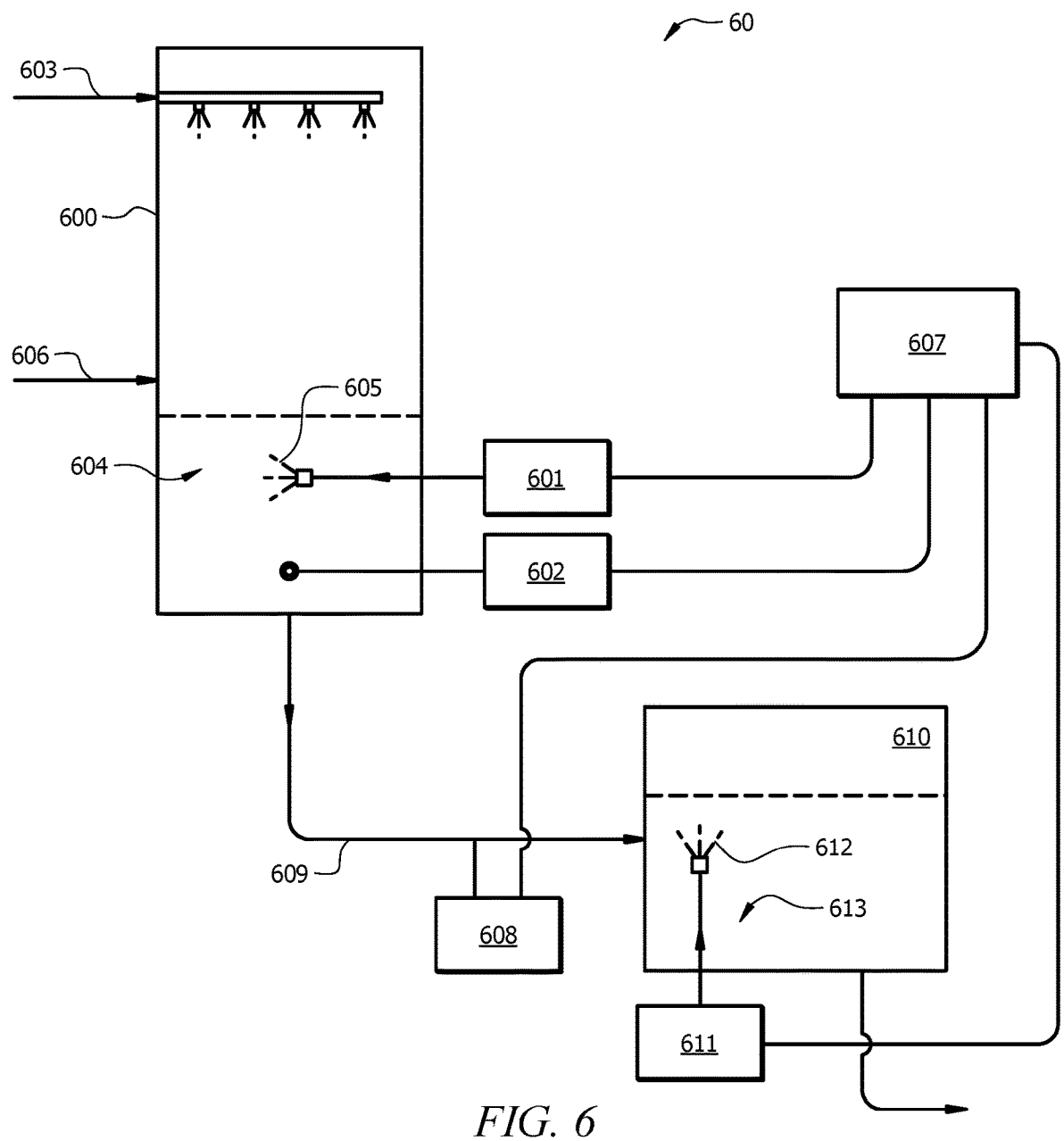
FIG. 6 shows a system for treating an emulsion emanating from a quenching process in the production of ethylene, according to embodiments of the invention.
Figure 7:
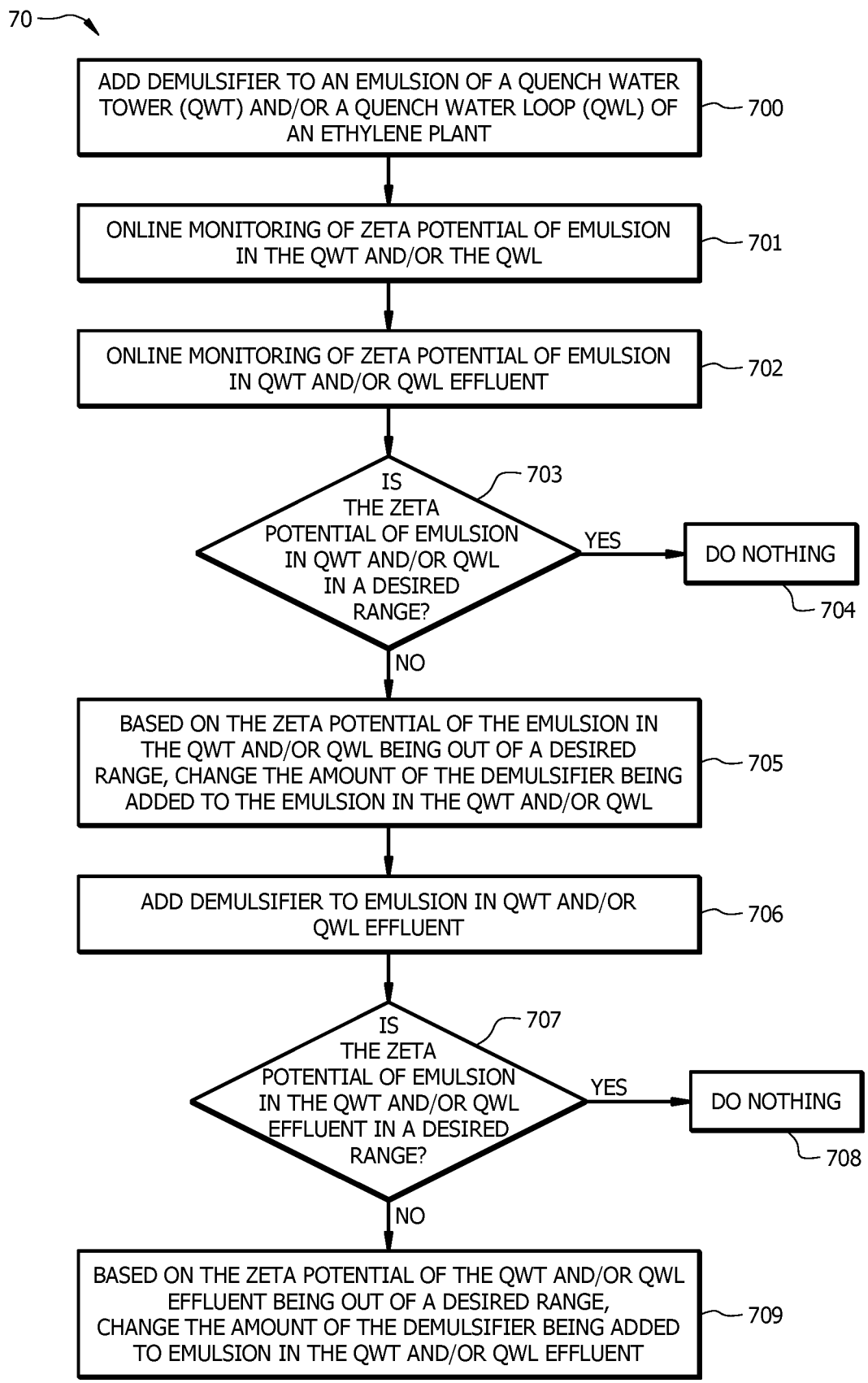
FIG. 7 shows a method that may be used for treating an emulsion emanating from a quenching process in the production of ethylene, according to embodiments of the invention.

FIG. 6 shows system 60 for treating an emulsion emanating from a quenching process in the production of ethylene, according to embodiments of the invention. FIG. 7 shows method 70 that may be used for treating an emulsion emanating from a quenching process in the production of ethylene, according to embodiments of the invention. Method 70 may be implemented using system 60. System 60 includes quench water tower 600, treating unit 601, online zeta potential monitor 602, controller 607, online zeta potential monitor 608, quench water settler 610, and treating unit 611. Cracked gas 606 flows from a steam cracking furnace into the bottom of quench water tower 600. Concurrently, quench water 603 is sprayed into the top of quench water tower 600. Contact between cracked gas 606, condensed dilution steam, and quench water 603 forms emulsion 604 in quench water tower 600.

Treating unit 601 treats emulsion 604 in quench water tower 600 with demulsifier 605. Thus, treating unit 601 may be used to implement an aspect of method 70, namely adding demulsifier 605 to emulsion 604 in quench water tower 600 and/or a quench water loop, as shown at block 700 of FIG. 7. In embodiments of the invention, demulsifier 605 is added at a point in quench water tower 600 and/or the quench water loop such that demulsifier 605 is most effective in breaking emulsion 604. Depending on the design of quench water tower 600 and/or the quench water loop, the point of addition of demulsifier 605 may vary. For example, the point of addition of demulsifier 605 could be at the top half, bottom half, or center of quench water tower 600 and/or the quench water loop. Tests may be carried out to determine what point of addition of demulsifier 605 to quench water tower 600 and/or quench water loop is most effective in breaking emulsion 604. Online zeta potential monitor 602 is similar to online zeta potential monitor 202, and thus, online zeta potential monitor 602 can automatically make zeta potential measurements of emulsion 604 in quench water tower 600 and/or the quench water loop (block 701), in a manner described above in relation to online zeta potential monitor 202 and quench water tower 200.

Online zeta potential monitor 608 is similar to online zeta potential monitor 602. However, online zeta potential monitor 608 automatically makes zeta potential measurements of quench water tower effluent 609.

FIG. 6 shows online zeta potential monitor 602 is in a reactive configuration in relation to the treating unit 601. However, alternatively or additionally, in embodiments of the invention, one or more online zeta potential monitors may be upstream of treating unit 601, in a predictive configuration in relation to the treating unit 601. Further, FIG. 6 shows online zeta potential monitor 608 is in a predictive configuration in relation to the treating unit 601. However, alternatively or additionally, in embodiments of the invention, one or more online zeta potential monitors may be downstream of treating unit 601, in a reactive configuration in relation to the treating unit 601.

Measurements of the zeta potential of emulsion 604 are used to change the amount of demulsifier 605 being added to emulsion 604 such that the amount of demulsifier is effective in breaking emulsion 604. For example, in embodiments of the invention, after online zeta potential monitor 602 automatically makes the measurements of the zeta potential of emulsion 604, the measurements are sent to a processor of a computer (e.g. processor or controller 607) that analyzes whether the dosing rate of demulsifier 205 is optimal, at block 703. Specifically, controller 607 may determine whether the zeta potential is within a desired range (e.g. a range in which emulsion 604 is least stable and in which demulsifier 605 is most effective in breaking emulsion 604). If the zeta potential is within the desired range, block 704 provides that nothing is done. If the zeta potential is not within the desired range, at block 705, controller 607 instructs treating unit 601 to change the dosing rate of demulsifier 605 to put the zeta potential of emulsion 604 in the desired range and thereby achieve an effective dosing rate for breaking emulsion 604.

Measurements of the zeta potential of quench water tower effluent 609 are used to change the amount of demulsifier 612 being added to emulsion 613 such that the amount of demulsifier is effective in breaking emulsion 613. For example, in embodiments of the invention, measurements of the zeta potential of quench water effluent 614 are automatically made by online zeta potential monitor 608 (block 702). Treating unit 611 treats emulsion 613 in quench water settler 610 with demulsifier 612. Thus, treating unit 611 may be used to implement an aspect of method 70, namely adding demulsifier 612 to emulsion 613, of quench water tower effluent 609, in quench water settler 610, as shown at block 706 of FIG. 7.

The measurements of zeta potential performed at block 702 are sent to a processor of a computer (e.g. processor or controller 607) that analyzes whether the dosing rate of demulsifier 612 is optimal (block 707). Specifically, controller 607 may determine whether the zeta potential is within a desired range (e.g. a range in which demulsifier 612 will be effective in breaking emulsion 613, since zeta potential monitor 608 is in a predictive orientation). If the zeta potential is within the desired range, block 708 provides that nothing is done. If the zeta potential is not within the desired range, at block 709, controller 607 instructs treating unit 601 to change the dosing rate to put the zeta potential of emulsion 613 in the desired range and thereby achieve an effective dosing rate for breaking emulsion 613. It should be noted that in embodiments of the invention, demulsifier 612 may be added to quench water effluent 609 after it has been monitored by online zeta potential monitor 608 but before it is fed to quench water settler 610. Method 70, or aspects thereof, may be repeated as often as required and at whatever interval is desired.

Although embodiments of the present invention have been described with reference to blocks of FIGS. 3, 5, and 7, it should be appreciated that operation of the present invention is not limited to the particular blocks and/or the particular order of the blocks illustrated in FIGS. 3, 5, and 7. Accordingly, embodiments of the invention may provide functionality as described herein using various steps in a sequence different than that of FIGS. 3, 5, and 7. The present invention will be described in greater detail by way of specific examples. The following examples are offered for illustrative purposes only, and are not intended to limit the invention in any manner. Those of skill in the art will readily recognize a variety of noncritical parameters, which can be changed or modified to yield essentially the same results.

EXAMPLE 1

Zeta Potential Measurements of Process Water at an Ethylene Production Plant

To illustrate the relationship of zeta-potential to emulsion breaker dosing rates, tests were carried out on a process water sample from a quench water tower loop of an ethylene plant. The zeta potential measurements were offline measurements. Table 1 presents the distribution within the organics in the water. The recovery was calculated using an internal standard. The total organics in the process water was about 1900 ppm (0.19 wt. %). A high molecular cationic emulsion breaker (polyDADMAC, Nalco Chemical Company, U.S.A.) was added at different concentrations to the process water sample. Then, the zeta potentials of the process water at the different concentrations of emulsion breaker were measured. FIG. 1 shows the results of these tests. FIG. 1 is a plot of the zeta potential of the process water versus the amount of cationic emulsion breaker added to the process water.

TABLE 1

| RI | Name | % in dispersed organic phase |
| --- | --- | --- |
| 930 | Cyclopentadiene | 0.50 |
| 1624 | Benzene | 20 |
| 2260 | Toluene | 12 |
| 2636 | Unknown | 0.18 |
| 2808 | Et-Benzene | 2.5 |
| 2852 | m/p-Xylene | 3.9 |
| 2940 | Styrene | 22 |
| 2984 | o-Xylene | 5.9 |
| 3260 | 2-Propenyl-Benzene | 0.42 |
| 3316 | n-Prop-Benzene | <0.01 |
| 3348 | 1-Et-(3 and 4)-Me-Benzene | 1.1 |
| 3388 | 1,3,5-TriMe-Benzene | 0.40 |
| 3420 | Phenol | 3.1 |
| 3444 | a-Me-Styrene | 0.85 |
| 3508 | Ethenyl-Me-Benzene | 5.3 |
| 3520 | 1,2,4-TriMe-Benzene | <0.01 |
| 3602 | Indane | <0.01 |
| 3652 | 1,2,3-TriMe-Benzene; Bleed | <0.01 |
| 3656 | 1,2,3-TriMe-Benzene | 0.89 |
| 3760 | Indene | 6.9 |
| 3766 | $C_4$-Benzene (triple bond) isomers | 0.10 |
| 3938 | Tetrahydro-DCPD | 0.50 |
| 4162 | Me-DihydroDCPD isomers | 0.63 |
| 4202 | Me-tetrahydro-DCPD | 0.18 |
| | Total | 88 |

As the results in FIG. 1 show, the initial zeta potential of the process water is very negative, about −90 mV. But when 0.5 and 1 ppm of emulsion breaker is added, the zeta potential increases to about 0 mV, which is optimal for emulsion breaking. When the amount of emulsion breaker is increased to 2 ppm, the zeta potential increases to 40 mV, which is relatively high. This relatively high zeta potential indicates that the emulsion is stable again. In practice, the emulsion breaker used in this test is regularly used to dose process water in quench water tower loops at 3 to 4 ppm. Thus, the test illustrates that overdosing with emulsion breakers often occurs in practice. The test further shows that making online zeta potential measurements is a valuable source of information about the state of hydrocarbon/water emulsion and how an emulsion breaker dosing rate may be implemented to break the emulsion. Viewing the graph of FIG. 1, an optimal range for zeta potential may be −30 mV and +30 mV.

It is claimed:

1. A method for treating an emulsion emanating from a quenching process in production of ethylene, the method comprising:
adding a demulsifier to a hydrocarbon/water emulsion;
online monitoring of zeta potential of the hydrocarbon/water emulsion; and
in response to the online monitoring of zeta potential, changing the amount of demulsifier being added to the hydrocarbon/water emulsion such that the amount of demulsifier is effective in breaking the emulsion;
wherein the emulsion comprises a dispersed oil phase and the continuous aqueous phase;
wherein the demulsifier comprises at least one member selected from the group consisting of polyalkylenepolyamine, epichlorohydrin dimethylamine, dimethylaminoethylacrylate methyl chloride salt, dimethylaminoethylmethacrylate methyl chloride salt, dimethylaminoethylmethacrylate methyl sulfate salt, dimethylaminoethylmethacrylate benzyl chloride salt, dimethylaminoethylacrylate methyl sulfate salt, dimethylaminoethylacrylate benzyl chloride salt, methacrylamidopropyl trimethylammonium chloride and acrylamidopropyl trimethylammonium chloride.

2. The method of claim 1, wherein the amount of demulsifier is changed so that the zeta potential of the emulsion is within a range of −30 to +30 mV.

3. The method of claim 1, wherein the amount of demulsifier is changed so that the zeta potential of the emulsion is within a range of −5 to +5 mV.

4. The method of claim 1, further comprising:
monitoring of one or more physicochemical parameters of the hydrocarbon/water emulsion.

5. The method of claim 4, wherein the hydrocarbon/water emulsion is in a quench water tower and/or a quench water loop in use for ethylene production.

6. The method of claim 4, further comprising:
in response to the monitoring of the one or more physicochemical parameters and the online monitoring of zeta potential, changing the amount of demulsifier being added to the hydrocarbon/water emulsion such that the amount of demulsifier is effective in breaking the emulsion.

7. The method of claim 1, wherein the demulsifier comprises at least one member selected from the group consisting of polyalkylenepolyamine, epichlorohydrin dimethylamine, dimethylaminoethylacrylate methyl chloride salt, dimethylaminoethylmethacrylate methyl chloride salt, dimethylaminoethylmethacrylate benzyl chloride salt, dimethylaminoethylacrylate methyl sulfate salt, dimethylaminoethylacrylate benzyl chloride salt, methacrylamidopropyl trimethylammonium chloride and acrylamidopropyl trimethylammonium chloride.

8. The method of claim 1, wherein the demulsifier comprises at least one member selected from the group consisting of a quaternary ammonium salt, a quaternized alkanolamine ester, a polyethylene glycol/polypropylene glycol triblock copolymer derivative of an amine, a polyamine, an alkoxylated or polyalkoxylated derivatives of an amine, a polyethylene imine, a polycyanoguanidine and a polyaluminum chloride silicate.

9. The method of claim 1, wherein the demulsifier comprises a cationic demulsifier.

10. A method for treating an emulsion emanating from a quenching process in production of ethylene, the method comprising:
adding a first demulsifier to a hydrocarbon/water emulsion in a quench water tower and/or a quench water loop in use for ethylene production;
online monitoring of zeta potential of the hydrocarbon/water emulsion in the quench water tower and/or quench water loop; and
in response to the online monitoring of zeta potential of the hydrocarbon/water emulsion, changing the amount of the first demulsifier being added to the hydrocarbon/water emulsion in the quench water tower and/or quench water loop;
flowing effluent from the quench water tower and/or the quench water loop to a quench water settler;
online monitoring of zeta potential of the effluent from the quench water tower and/or the quench water loop;
adding a second demulsifier to the effluent from the quench water tower and/or the quench water loop;
online monitoring of zeta potential of the effluent from the quench water tower and/or the quench water loop; and
in response to the online monitoring of zeta potential of the effluent, changing the amount of the second demulsifier being added to the effluent from the quench water tower and/or quench water loop;
wherein the first demulsifier comprises at least one member selected from the group consisting of polyalkylenepolyamine, epichlorohydrin dimethylamine, dimethylaminoethylacrylate methyl chloride salt, dimethylaminoethylmethacrylate methyl chloride salt, dimethylaminoethylmethacrylate methyl sulfate salt, dimethylaminoethylmethacrylate benzyl chloride salt, dimethylaminoethylacrylate methyl sulfate salt, dimethylaminoethylacrylate benzyl chloride salt, methacrylamidopropyl trimethylammonium chloride and acrylamidopropyl trimethylammonium chloride.

11. The method of claim 10, wherein the amount of the first demulsifier and the second demulsifier are changed so that the zeta potential of the hydrocarbon/water emulsion in the quench water tower and/or quench water loop and the zeta potential of the effluent from the quench water tower and/or the quench water loop are within a range of −30 to +30 mV.

12. The method of claim 10, wherein the amount of the first demulsifier and the second demulsifier are changed so that the zeta potential of the hydrocarbon/water emulsion in the quench water tower and/or quench water loop and the zeta potential of the effluent from the quench water tower and/or the quench water loop are within a range of −5 to +5 mV.

13. The method of claim 10, wherein the first demulsifier comprises at least one member selected from the group consisting of polyalkylenepolyamine, epichlorohydrin dimethylamine, dimethylaminoethylmethacrylate methyl chloride salt, dimethylaminoethylmethacrylate methyl sulfate salt, dimethylaminoethylmethacrylate benzyl chloride salt, dimethylaminoethylacrylate methyl sulfate salt, dimethylaminoethylacrylate benzyl chloride salt, methacrylamidopropyl trimethylammonium chloride and acrylamidopropyl trimethylammonium chloride.

14. The method of claim 10, wherein the first demulsifier is added at a point in the quench water tower and/or the quench water loop such that the demulsifier is effective in breaking the hydrocarbon/water emulsion in the quench water tower and/or the quench water loop.

15. The method of claim 10, wherein the second demulsifier is added to the effluent from the quench water tower and/or quench water loop in the quench water settler.

16. The method of claim 10, wherein the second demulsifier comprises at least one member selected from the group consisting of polyalkylenepolyamine, epichlorohydrin dimethylamine, dimethylaminoethylacrylate methyl chloride salt, dimethylaminoethylmethacrylate methyl chloride salt, dimethylaminoethylmethacrylate methyl sulfate salt, dimethylaminoethylmethacrylate benzyl chloride salt, dimethylaminoethylacrylate methyl sulfate salt, dimethylaminoethylacrylate benzyl chloride salt, methacrylamidopropyl trimethylammonium chloride and acrylamidopropyl trimethylammonium chloride.

17. The method of claim 10, wherein at least one of the first demulsifier and second demulsifier comprises a cationic demulsifier.

18. The method of claim 10, wherein the first demulsifier and second demulsifier are different.

19. The method of claim 10, wherein the first demulsifier and second demulsifier are same.

* * * * *